United States Patent
Van Sickle et al.

(10) Patent No.: US 6,660,712 B2
(45) Date of Patent: Dec. 9, 2003

(54) STABILIZATION OF AMIDO ACIDS WITH ANTIOXIDANTS

(76) Inventors: Dale Elbert Van Sickle, 2113 Sheffield St., Kingsport, TN (US) 37660-4721; George Chester Zima, 1000 University Blvd. F45, Kingsport, TN (US) 37660; Jeffrey Scott DuPont, 1012 Seibel La., Cincinnati, OH (US) 45238; Robert Richard Dykstra, 7715 Mitchell Park Dr., Cleves, OH (US) 45002

( * ) Notice: Subject to any disclaimer, the term of this patent is extended or adjusted under 35 U.S.C. 154(b) by 0 days.

(21) Appl. No.: 09/870,995

(22) Filed: Jun. 1, 2001

(65) Prior Publication Data

US 2002/0103101 A1 Aug. 1, 2002

Related U.S. Application Data

(60) Provisional application No. 60/208,502, filed on Jun. 2, 2000.

(51) Int. Cl.[7] .............................. C11D 7/26; C11D 7/32; C11D 7/22
(52) U.S. Cl. ........................................ 510/501; 510/402
(58) Field of Search .................................. 510/310, 309, 510/370, 372, 376, 402, 501

(56) References Cited

U.S. PATENT DOCUMENTS

| | | |
|---|---|---|
| 4,468,476 A | 8/1984 | Yang et al. |
| 4,634,551 A | 1/1987 | Burns et al. |
| 4,681,695 A | 7/1987 | Divo |
| 4,852,989 A | 8/1989 | Burns et al. |
| 5,391,780 A | 2/1995 | Zima et al. |
| 5,391,783 A | 2/1995 | Colignon et al. |
| 5,393,901 A | 2/1995 | Zima et al. |
| 5,393,905 A | 2/1995 | Zima et al. |
| 5,414,099 A | 5/1995 | Heinzman |
| 5,429,773 A | 7/1995 | Sherry et al. |
| 5,466,840 A | 11/1995 | Lutz et al. |
| 5,523,434 A | 6/1996 | Burns et al. |
| 5,534,194 A | 7/1996 | Borland et al. |
| 5,534,195 A | 7/1996 | Chapman et al. |
| 5,534,196 A | 7/1996 | Chapman et al. |
| 5,650,527 A | 7/1997 | Lutz et al. |
| 5,674,828 A * | 10/1997 | Knowlton et al. .......... 510/372 |
| 5,712,239 A * | 1/1998 | Knowlton et al. .......... 510/372 |
| 5,717,118 A | 2/1998 | Lutz et al. |
| 6,103,685 A * | 8/2000 | Hall |

FOREIGN PATENT DOCUMENTS

| | | |
|---|---|---|
| EP | 0 402 339 A1 | 12/1990 |
| EP | 0 415 472 A2 | 3/1991 |
| EP | 0 484 634 A1 | 5/1992 |
| GB | 2 249 104 A | 4/1992 |
| GB | 2323385 * | 9/1998 |
| JP | 6-179648 | 6/1994 |
| JP | 6-306042 | 11/1994 |
| JP | 7-228566 | 8/1995 |
| JP | 8-245549 | 9/1996 |
| JP | 9-110824 | 4/1997 |
| WO | WO 89/08718 | 9/1989 |
| WO | WO 94/18159 | 8/1994 |
| WO | WO 94/28104 | 12/1994 |
| WO | WO 95/07882 | 3/1995 |
| WO | WO 95/07883 | 3/1995 |
| WO | WO 96/16148 | 5/1996 |
| WO | WO 97/27280 | 7/1997 |
| WO | WO 99/09004 | 2/1999 |

OTHER PUBLICATIONS

Lock et al, J. Chemical Society (B), (1966) pp. 690–696.
Sager, J. Chemical Society (B), (1967), pp. 428–439.
Sager, J. Chemical Society (B), (1967), pp. 1047–1061.

* cited by examiner

Primary Examiner—Gregory Delcotto

(57) ABSTRACT

The invention relates to stabilized amido acid compositions. More particularly, the invention relates to compositions of amido acids, such as 6-nonanoylamidohexanoic acid, stabilized with antioxidants. The stabilized amido acid compositions are useful in the manufacture of bleach activators such as sodium nonanamidohexanoyloxybenzenesulfonate. Bleach activators made from the stabilized amido acids of the invention are capable of possessing improved coloration.

12 Claims, No Drawings

STABILIZATION OF AMIDO ACIDS WITH ANTIOXIDANTS

This application claims priority under 35 U.S.C. §119 to provisional application Ser. No. 60/208,502, filed Jun. 2, 2000, which is incorporated herein by reference.

FIELD OF THE INVENTION

The invention relates to stabilized amido acid compositions. More particularly, the invention relates to compositions of amido acids, such as 6-nonanoylamidohexanoic acid, stabilized with antioxidants. The stabilized amido acid compositions are useful in the manufacture of bleach activators such as sodium nonanamidohexanoyloxybenzenesulfonate. Stablization of the amido acid protects chemical degradation. Additionally, bleach activators made from the stabilized amido acids of the invention possess improved color.

BACKGROUND

Hypochlorite and hydrogen peroxide are well known for their bleaching properties. As a bleaching agent in laundry detergents, hydrogen peroxide has the advantage of being safe to use with many fabric dyes. However, hydrogen peroxide bleaches are not effective at temperatures below 50° C. This limits their use as most laundering is carried out at temperatures below about 40° C. For this reason, various peroxyacids were developed as alternative bleaching agents for use in laundry detergents. The peroxyacids were generally found to be effective bleaching agents at the lower laundering temperatures. Because of their chemical instability and potential safety hazards, however, peroxyacids themselves are generally unsuitable for storage and handling.

Bleach activators were developed to address storage and handling concerns associated with peroxyacids. Bleach activators have the ability to hydrolyze under laundering conditions, effectively producing peroxyacids, even at lower temperatures, e.g. below 40° C. By perhydrolyzing bleach molecules, bleach activators enhance the activity, and thus the cleaning ability, of a laundry detergent. Bleach activators have the further advantage of being stable when stored in solid form at room temperature. These properties permit the use of bleach activators in a wide variety of laundry detergents and other cleaning formulations.

An important class of bleach activators is phenyl ester salts. An effective bleach activator, phenyl ester salts readily react with bleach to form the corresponding peroxyacid. Exemplary phenyl ester salts, which are used as bleach activators, and their preparation are described in U.S. Pat. Nos. 4,634,551; 4,852,989; 5,391,780; 5,393,905; 5,393,901; 5,414,099; 5,466,840; 5,523,434; 5,650,527; and 5,717,118; as well as in published PCT applications WO 94/18159, WO 95/07883, WO 96/16148, and WO 99/09004. These U.S. Patents and published PCT applications are incorporated herein in their entirety.

Bleach activating phenyl ester salts can be prepared in various ways. For example, sodium nonanamidohexanoyloxybenzenesulfonate can be prepared by reacting a Cg fatty acid, and caprolactam to form 6-nonanoylamidohexanoic acid. Sodium p-hydroxybenzenesulfonate and acetic anhydride are then reacted with the nonanoylamidohexanoic acid (an amido acid) in a solvent to form sodium nonanamidohexanoyloxybenzenesulfonate. This reaction mechanism is shown below in equations 1A and 1B.

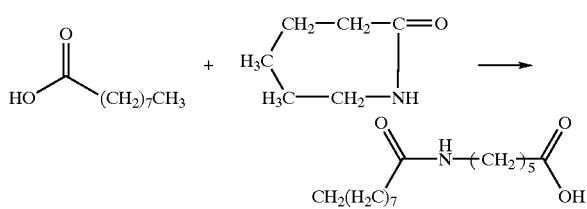

Equation 1A

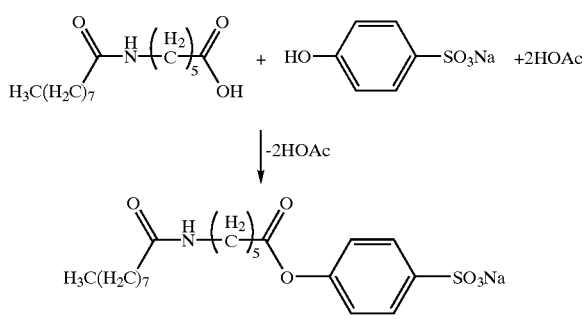

Equation 1B

The major difficulty with such a reaction is the formation of unwanted colored by-products. As such, the final product can possess a commercially undesirable non-white appearance. The formation of these non-white, colored by-products are believed to be due in large part to the oxidation of the amido acid intermediate formed during the process. Such an oxidation process may be similar to the oxidation of N-alkylamides, as described by Sager: M. V. Lock and B. F. Sager, J. Chem. Soc. (B), (1966), 690, B. F. Sager, J. Chem. Soc. (B), (1967), 428, and B. F. Sager, J. Chem. Soc. (B), (1967), 1047. Oxidation of the amido acid intermediate causes the formation of unwanted color as well as chemical degradation of the amido acid—both of which are undesirable.

The removal of unwanted colored by-products from the commercial phenyl ester salts is difficult and expensive. Indeed, current techniques for removing color from phenyl ester salts, such as sodium nonanamidohexanoyloxybenzenesulfonate, either fail to produce a colorless, commercially desirable, white product or require undue time and/or expense. For example, one technique used in forming amido acid phenyl esters involves sparging an inert gas through the amido acid reaction system. See, for example, U.S. Pat. No. 5,414,099. Another technique which has been described involves admixing a water-based purification system with an amido acid phenyl ester sulfonate reaction product to form a purification system and separating the purified phenyl ester salt from the purification system such that a percentage of the color forming impurities are removed. See, for example, published PCT Application WO 99/09004.

Accordingly, there is a need in the art for a simple, cost-effective means of forming precluding or lessening the formation of colored by-products during the synthesis of phenyl ester salts.

SUMMARY OF THE INVENTION

The invention answers the problems connected with forming substantially discoloration-free phenyl ester salts, which may be used as bleach activators. More particularly, commercially acceptable amido acids for use in the formation of bleach activating phenyl ester salts generally appear white and do not contain discolored amido acid by-products. By employing white amido acid products in the preparation of phenyl ester salts, a commercially acceptable phenyl ester salt can be prepared.

The invention aids in the prevention of discoloration and chemical degradation by providing stabilized liquid amido acid compositions. More specifically, the invention provides a stabilized liquid amido acid composition which contain at least one amido acid and an antioxidant. Additionally, the invention relates to processes of making a stabilized amido acid composition as well as processes for preparing an amido phenyl ester salt from an antioxidant stabilized amido acid.

DETAILED DESCRIPTION

According to the invention, amido acids can be stabilized to prevent or reduce their discoloration and chemical degradation. These stabilized amido acids are useful in the preparation of bleach activating, phenyl ester salts by processes known in the art. Simply put, the invention combines an antioxidant with an amido acid, typically a amido-carboxylic acid to form a stabilized amido acid. These stabilized amido acids may be used in the preparation of bleach activating amido phenyl ester salts which may be used in laundry detergents, fabric softeners, hard surface cleaners and other bleach-containing cleaning compositions.

Generally, discolored amido acid by-products and chemical degradation result from the absorption of oxygen by an amido acid product. The amido acid is particularly susceptible as a melt or in solution. To avoid the absorption of oxygen into a liquid amido acid product, an effective stabilizing amount of an antioxidant is added to an amido acid product. The presence of the antioxidant prevents or reduces the absorption of the oxygen such that the product does not become visibly discolored, e.g., a yellow or brownish coloration, or does not chemically degrade.

Amido Acids

The amido acids that can be stabilized through the use of the invention include amido-carboxylic acids. Exemplary amido-carboxylic acids include those represented by formulas I and II:

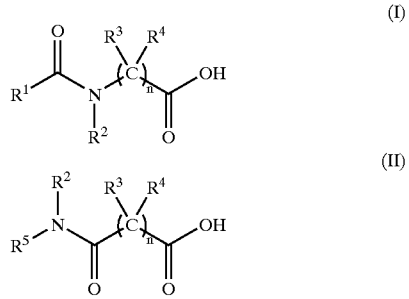

where $R^1$ is selected from $C_1$-$C_{22}$ alkyl, $C_2$-$C_{22}$ alkenyl, $C_2$-$C_{22}$ alkynyl, $C_3$-$C_{22}$ cycloalkyl, and $C_6$-$C_{14}$ aryl; $R^2$ and $R^5$ are each independently selected from hydrogen, $C_1$-$C_{22}$ alkyl, $C_2$-$C_{22}$ alkenyl, $C_2$-$C_{22}$ alkynyl, $C_3$-$C_{22}$ cycloalkyl, $C_6$-$C_{14}$ aryl, and where in formula II, $R^2$ and $R^5$ can together with the nitrogen carrying them form a $C_3$-$C_{10}$ heterocycle; $R^3$ and $R^4$ are each independently selected from hydrogen, $C_1$-$C_{10}$ alkyl, $C_2$-$C_{10}$ alkenyl, $C_2$-$C_{10}$ alkynyl, $C_3$-$C_{10}$ cycloalkyl, $C_6$-$C_{10}$ aryl and where $R^3$ and $R^4$ may together with the carbon carrying them form a $C_3$-$C_{10}$ cycloalkyl; and n is an integer from 0 to 20. The phrase "independently selected" means that the various radicals may or may not be the same. This phrase also means that when n is greater than 1, each $CR^3R^4$ group may or may not be the same.

Preferably, the individual substituents for the amido-carboxylic acids of formulas I and II are as follows: $R^1$ is selected from $C_5$-$C_{15}$ alkyl, $C_5$-$C_{15}$ alkenyl, $C_5$-$C_{15}$ alkynyl, $C_5$-$C_{15}$ cycloalkyl, and $C_6$-$C_{14}$ aryl; $R^2$ and $R^5$ are each independently selected from hydrogen, $C_5$-$C_{15}$ alkyl; $R^3$ and $R^4$ are each independently selected from hydrogen, $C_1$-$C_5$ alkyl, $C_2$-$C_5$ alkenyl, $C_2$-$C_5$ alkynyl, $C_3$-$C_6$ cycloalkyl, $C_6$-$C_{10}$ aryl and where $R^3$ and $R^4$ together with the carbon carrying them form a $C_3$-$C_6$ cycloalkyl; and n is an integer from 0 to 10.

More preferably the individual substituents for the amido-carboxylic acids of formulas I and II are as follows: $R^1$ is selected from $C_7$-$C_{11}$ alkyl; $R^2$ and $R^5$ are each independently selected from hydrogen and $C_7$-$C_{11}$ alkyl; $R^3$ and $R^4$ are each independently selected from hydrogen and $C_1$-$C_5$ alkyl n is an integer from 4 to 8. A particularly preferred amido acid is nonanamidohexanoic acid.

It is recognized that combinations of suitable, preferred and most preferred substituents can be used with the invention. For example, a preferred $R^1$ could be used in conjunction with a suitable $R^2$ and a most preferred $R^4$.

Antioxidants

Any antioxidant or mixture of antioxidants capable of stabilizing the amido acids may be employed in the invention. Examples of preferred antioxidants include, but are not limited to, 1,3,5-trimethyl-2,4,6-tris (3,5-di-tert-butyl-4-hydroxybenzyl) benzene (sold under the product name Ethanox 330® from the Albemarle Corporation), Tetrakis (methylene (3,5-di-tert-butyl-4-hydroxyhydrocinnamate)) methane (sold under the product name Irganox® by Ciba-Geigy), butylated hydroxytoluene (BHT), and mixtures thereof.

An effective amount of an antioxidant for stabilizing the amido acid is any amount capable of preventing the oxidation of the amido acid. Preferably the antioxidant is present in an amount that will not affect the preparation of a bleach activating phenyl ester salt or its properties. Typically, the antioxidant is present in the stabilized amido acid composition in an amount of up to 5 wt %, more preferably ranging from about 0.001 to about 2 wt % of the composition, more preferably about 0.01 to about 1 wt % and most preferably, about 0.01 to about 0.1 wt %.

Stabilized Amido Acid Compositions

Typically, the amido acids of the invention do not undergo oxidation when the amido acids are in a solid state. Yet, when the amido acids are in solution and/or are a liquid or molten state, the amido acids can become oxidized resulting in the formation of visibly discolored amido acid by-products. In contrast, the inventive stabilized amido acid compositions are those that do not become visibly discolored when placed in a liquid or molten state. The amido acid discoloration is determined under normal lighting conditions by the naked eye.

Generally, the stabilized amido acid compositions are stable to oxidation discoloration and/or chemical degradation at a temperature of about 100° C. for approximately 70 minutes. Preferably, the stabilized amido acid compositions do not become discolored when subjected to elevated temp for at least 120 minutes, more preferably 240 minutes and most preferably 72 hours or more. To determine whether the amido acid compositions are discolored, test samples of the amido acid compositions may be placed in tubes and then visually compared to colors of the platinum-cobalt scale contained in an adjacent tube.

The stabilized amido acid compositions can be in the form of a solid (typically crystalline), a melt or dissolved in a solvent. Although the stabilized amido acid can be stored as a solid, the stabilized amido acid is preferably stored as a liquid, e.g., a melt or a solution. A liquid form is preferred because it can be easily pumped to a reactor for conversion to a bleach activator. The use of solid, crystalline material is generally less preferred as the handling and continuous addition of a solid to a reaction process is more difficult than a liquid.

Process for Preparing Stabilized Compositions

The stabilized amido acid compositions of the invention may be formed by admixing the amido acids with an effective stabilizing amount of the antioxidant. The mixing of the two components may be accomplished by any conventional means. It is understood, however, that it is preferred that the amido acid is not subjected to temperatures far exceeding its melting point prior to its admixture with the antioxidant.

One suitable process for preparing the stabilized amido acid composition is to form a melt of the amido acid using a temperature slightly, 0–10° C., above the melting point of the amido acid. To this amido acid melt is admixed a stabilizing effective amount of the antioxidant. Another suitable process involves forming a solution of the amido acid, such as a solution of amido acid and sulfolane, and admixing the antioxidant to the amido acid solution. Yet another process that may be used involves forming a particulate or powdered mixture of the amido acid and admixing the antioxidant to the powdered amido acid. This protects the compositions from discoloration or degradation upon melting or dissolving. The process of preparing the stabilized amido acid compositions may be performed either as a batch or continuous process.

Phenol Ester Salts formed from the Stabilized Compositions

The stabilized amido acid compositions of the invention may be used to form bleach activating phenyl ester salts. The preparation of these phenyl ester salts is discussed above. Phenyl ester salts prepared with the stabilized amido acid compositions of the invention are preferably substantially free of amido acid discoloring by-products. Any bleach activating phenyl ester salt that can be formed from an amido acid may also be prepared through the use of the inventive stabilized amido acids.

Bleach Activated Compositions Containing Phenyl Ester Salts

The phenyl ester salts prepared from the stabilized amido acids of the invention may be formulated into a wide variety of bleach activated compositions. Typically, the bleach activated phenyl ester salts of the invention are employed in the formation of laundry detergents and hard surface cleaners. Due to their ability to release hydrogen peroxide in an aqueous solution, however, the phenyl ester salts provide particular utility in laundry detergents for the bleaching of textiles. The bleach activating phenyl ester salts may be formulated into a wide range of detergent compositions. Suitable detergent compositions for the phenyl ester salts of the invention are described in Burns et al., U.S. Pat. No. 4,852,989, Burns et al., U.S. Pat. No. 4,634,551, Chapman et al., U.S. Pat. No. 5,534,194, Chapman et al., U.S. Pat. No. 5,534,195 and Guedira et al., WO 96/16148, herein incorporated by reference in their entirety.

The following examples are intended to illustrate, but not limit, the scope of the present invention.

EXAMPLES

Example 1A

Preparation of Recrystallized Amido Acid

Crude 6-nonanoylamidohexanoic acid (200.4 g) was filly dissolved in 300 mL boiling methanol to give a brown solution and then cooled overnight in a refrigerator at approximately 0° C. The resulting cake was broken up into a slurry that was filtered on a coarse glass frit and washed with 100 mL room temperature methanol to give a white product and brown filtrate and washings. 130.6 g amido acid was recovered from the glass frit. The product was determined to have a melting point of 79.06° C. by differential scanning calorimetry (DSC) and a heat of fusion of 40.68 cal/g.

Example 1B

Preparation of Recrystallized Amido Acid

Amido acid (70.28 g) was recovered from the methanol filtrate and washings of Example 1A by evaporation.

Example 1C

Preparation of Recrystallized Amido Acid

Repeat the recrystallization of Example 1A with 200 g crude amido acid.

Example 1D

Preparation of Recrystallized Amido Acid

Repeat the recrystallization of Example 1A with 150 g crude amido acid and 200 mL methanol. The solution was cooled to about 2° C. and the resulting solid was washed with about 30 mL −20° C. methanol. The yield was 119.06 g of white product.

Example 1E

Preparation of Recrystallized Amido Acid

Repeat the recrystallization of Example 1A with 400 g crude amido acid and 500 mL methanol. The solution was cooled to about 2° C. and the resulting solid was sparsely washed with −20° C. methanol. The yield was 278.76 g.

Example 2

Oxidation of Crystalline or Molten Amido Acid Without Antioxidant

Recrystallized amido acid (3.00 g) was placed in each of two 250 mL Schott bottles, each of which fit snugly in a GlassCol heating mantle. The temperature was held at either 80° C. (crystalline) or 100° C. (melt) for 24 hours using a Eurotherm/thermocouple assembly to maintain the temperature. Oxygen absorption was measured using a MicroOxymax with one atmosphere of air. The oxygen consumption of various amido acid samples was determined by the MicroOxymax (Columbus Instruments, Columbus, Ohio) which is a closed-circuit respirator used to measure minute amounts of oxygen consumed by a sample.

Strong oxygen absorption was observed for the melt, but negligible absorption was observed for the crystalline sample. The melt showed an initial accelerating oxygen absorption. Specifically, at 14 hours an absorption of 1800 uL was observed, at 23 hours an absorption of 3740 uL was observed and at 26 hours an absorption of 4100 uL was observed.

Example 3

Oxidation of an Amido Acid Melt With or Without Antioxidant

Recrystallized amido acid (3.00 g) from Example 1D was placed in each of two 250 mL Schott bottles, each of which fit snugly in a GlassCol heating mantle. To one of the bottles, 3.6 mg Ethanox 330, a high molecular weight phenolic antioxidant (mw 774), was added before connecting the apparatus to a MicroOxymax with one atmosphere of air. The temperature was held at 100° C. for 80 hours using a Eurotherm/thermocouple assembly to maintain this temperature for both bottles. At the end of the 80 hour test, the MicroOxymax detected about 8250 uL oxygen absorption for the uninhibited sample and less than 250 uL oxygen absorption for the Ethanox 330 sample. The Ethanox 330 amido acid sample remained white, wherein the unstabilized amido acid sample exhibited a strong brown color.

The experiment was repeated using 3.32 g recrystallized amido acid from Example 1D and 6.1 mg Ethanox 330. The sample was placed in a glass bulb apparatus under 36.5 psig of pure oxygen. Holding the temperature at 160° C. for 70 min. resulted in a brown melt.

Example 4

Oxidation of an Amido Acid Melt With or Without Antioxidant

Recrystallized amido acid (3.02 g) was placed in each of two 250 mL Schott bottles, each of which fit snugly in a GlassCol heating mantle. 10.6 mg food grade BHT (2,6-di-tert-butyl-4-methylphenol) was added to one of the bottles and mixed on a steam table before connecting the apparatus to a MicroOxymax apparatus with one atmosphere of air. The temperature was held at 100° C. for 24 hours using a Eurotherm/thermocouple assembly to maintain this temperature for both bottles.

The uninhibited sample showed strong oxidation with the MicroOxymax showing approximately 9,100 uL oxygen absorption over 64 hours. The BHT-inhibited sample, however, showed no oxidation.

Example 5

Oxidation of an Amido Acid Melt and a Methyl Ester Melt Without Antioxidant

A methyl ester of the amido acid was synthesized by mixing 100.09 g amido acid from Example 1E with 150 mL methylene chloride and 47 mL thionyl chloride. The mixture was allowed to stand overnight. The next day excess methylene chloride and thionyl chloride were removed by vacuum. A portion of the crude acid chloride (67.82 g) was treated with 100 mL methanol with stirring at room temperature for two hours. Excess methanol was removed by heating to 80° C. at 20 Torr. The product had an odor, possibly $SO_2$.

The oxidation experiment of Example 2 was repeated using two 3.0 g amido acid samples from Example 1D. Oxidation was measured for either 30 hours or 63 hours at 100° C. Strong oxidation of the amido acid was observed.

In contrast, two 3.0 g samples of the methyl ester of the amido acid was measured for oxidation for 30 hours and at 63 hours at 100° C. No oxidation was observed. The results of the MicroOxymax tests are shown below:

TABLE 1

| Sample | Time (hrs) | Total $O_2$ uL |
|---|---|---|
| Amido Acid | 30 | 4858 |
| Methyl Ester | 30 | 65 |

TABLE 1-continued

| Sample | Time (hrs) | Total $O_2$ uL |
|---|---|---|
| Amido Acid | 63 | 9400 |
| Methyl Ester | 63 | 42 |

Example 6

Oxidation of an Amido Acid Melt Without Antioxidant

The experiment of Example 2 was repeated using 10.02 g amido acid. Oxidation was performed under about 35–41 psig of pure oxygen in a glass bulb apparatus, not a MicroOxymax. Oxidation was measured over 1786 min. A 5.6% decomposition of the amido acid occurred and a yellow/brown coloration of the amido acid product was observed.

The 5.6% decomposition was calculated as follows: 10.02 g amido acid was placed into the glass bulb. The glass bulb with the amido acid weighed 86.4009 prior to testing and 86.3344 after having heated the bulb for the 1786 minutes. Thus, there was a 66.5 mg oxygen weight gain (86.4009–86.334=0.0665 g=66.5 mg) in the amido acid which corresponds to absorption of 2.08 mmole $O_2$. The 2.08 mmole $O_2$ represents a 5.6% conversion of the 36.92 mmoles of amido acid.

As depicted in Table 2 below, the data from the glass bulb test was measured at ten different data points.

TABLE 2

| Data Point | Time (Min.) | Tank Temp. (° C.) | Bulb Temp. (° C.) | Pressure Gauge |
|---|---|---|---|---|
| 1 | 0 | 24.0 | 101.2 | 41.3 |
| 2 | 1 | 24.0 | 100.9 | 41.1 |
| 3 | 5 | 24.0 | 100.8 | 41.1 |
| 4 | 70 | 24.0 | 100.8 | 41.0 |
| 5 | 110 | 24.8 | 100.8 | 40.8 |
| 6 | 245 | 25.0 | 100.7 | 40.3 |
| 7 | 1386 | 24.5 | 101.0 | 35.9 |
| 8 | 1450 | 24.5 | 100.9 | 35.6 |
| 9 | 1615 | 24.0 | 100.6 | 35.3 |
| 10 | 1788 | 25.0 | 100.6 | 35.0 |

Example 7

Oxidation of an Amido Acid Melt Without Antioxidant

The experiment of Example 6 was repeated using 120° C. and 19.97 g amido acid (mw 271) from Example 1A. Oxidation was measured at various intervals over 250 min. A 4.8% decomposition of the amido acid occurred and a light brown coloration of the amido acid product was observed.

The 4.8% decomposition was calculated as follows: 19.97 g amido acid was placed into the glass bulb. The glass bulb with the amido acid weighed 96.3984 prior to testing and 96.2846 after having heated the bulb for the 250 minutes. Thus, there was a 113.8 mg oxygen weight gain in the amido acid, which corresponds to absorption of 3.56 mmole $O_2$. The 3.56 mmole $O_2$ represents a 4.8% conversion of the 73.58 mmoles of amido acid.

As depicted in Table 3 below, the data from the glass bulb test was measured at eleven different data points.

TABLE 3

| Data Point | Time (Min.) | Tank Temp. (° C.) | Bulb Temp. (° C.) | Pressure Gauge |
|---|---|---|---|---|
| 1 | 0 | 23 | 121.5 | 37.7 |
| 2 | 2 | 23 | 121.3 | 37.5 |
| 3 | 5 | 23 | 121.0 | 37.4 |
| 4 | 15 | 23 | 121.0 | 37.1 |
| 5 | 55 | 23 | 121.0 | 35.4 |
| 6 | 80 | 23 | 121.0 | 34.0 |
| 7 | 110 | 23 | 121.0 | 32.5 |
| 8 | 126 | 23 | 121.0 | 31.8 |
| 9 | 203 | 23 | 121.0 | 29.3 |
| 10 | 240 | 23 | 121.0 | 28.4 |
| 11 | 250 | 23 | 121.0 | 28.0 |

Example 8

Oxidation of an Amido Acid Melt Without Antioxidant

The experiment of Example 7 was repeated using 20.12 g of nearly pure white amido acid. Oxidation was measured over 430 min. It was found that 5.50 mmol of $O_2$ was absorbed with 7.42% decomposition of the amido acid. The amido acid had a light brown coloration.

The 7.42% decomposition was calculated as follows: 20.12 g amido acid was placed into the glass bulb. The glass bulb with the amido acid weighed 96.6017 prior to testing and 96.4258 after having heated the bulb for the 430 minutes. Thus, there was a 175.9 mg oxygen weight gain in the amido acid, which corresponds to absorption of 5.50 mmole $O_2$. The 5.50 mmole $O_2$ represents a 7.42% conversion of the amido acid.

As depicted in Table 4 below, the data from the glass bulb test was measured at eleven different data points.

TABLE 4

| Data Point | Time (Min.) | Tank Temp. (° C.) | Bulb Temp. (° C.) | Pressure Gauge |
|---|---|---|---|---|
| 1 | 0 | 24.1 | 121.8 | 42.1 |
| 2 | 2 | 24.1 | 121.6 | 42.0 |
| 3 | 5 | 24.1 | 121.4 | 41.9 |
| 4 | 14 | 24.1 | 121.2 | 41.6 |
| 5 | 55 | 24.1 | 121.2 | 39.7 |
| 6 | 85 | 24.0 | 121.3 | 37.9 |
| 7 | 170 | 23.5 | 121.1 | 33.4 |
| 8 | 276 | 23.0 | 121.4 | 30.5 |
| 9 | 330 | 23.5 | 121.2 | 29.5 |
| 10 | 375 | 23.1 | 121.2 | 28.7 |
| 11 | 430 | 23.1 | 121.1 | 28.0 |

Example 9

Oxidation of an Amido Acid Melt Without Antioxidant

The experiment of Example 2 was repeated using 10.01 g amido acid of Example 1D, except the temperature was maintained at 100° C. for 2820 min and also maintained at 120° C. for 3000 min. The amido acid melt readily oxidized at the 100–120° C. temperatures. 2.95 mmol $O_2$ was absorbed with a yellow/brown coloration observed. This oxygen absorption was calculated as follows: The weight of the bulb and amido acid prior to absorption was 86.43 g and after absorption the bulb and amido acid weight 86.3356 grams. Thus the amido acid absorbed 94.4 mg of oxygen which is 2.95 mmol $O_2$.

As depicted in Table 5 below, the data from the glass bulb test at 100° C. was measured at eleven different data points.

TABLE 5

| Data Point | Time (Min.) | Tank Temp. (° C.) | Bulb Temp. (° C.) | Pressure Gauge |
|---|---|---|---|---|
| 1 | 0 | 25.1 | 101.0 | 41.8 |
| 2 | 2 | 25.1 | 100.9 | 42.0 |
| 3 | 5 | 25.1 | 100.6 | 41.9 |
| 4 | 40 | 25.0 | 100.4 | 41.9 |
| 5 | 104 | 25.0 | 100.5 | 41.8 |
| 6 | 1320 | 25.0 | 100.8 | 38.8 |
| 7 | 1410 | 25.0 | 100.6 | 38.6 |
| 8 | 1750 | 25.0 | 100.4 | 38.3 |
| 9 | 1840 | 25.0 | 100.4 | 38.3 |
| 10 | 2790 | 23.8 | 100.9 | 37.5 |
| 11 | 2820 | 24.0 | 100.4 | 37.5 |

As depicted in Table 6 below, the data from the glass bulb test at 120° C. was measured at twelve different data points.

TABLE 6

| Data Point | Time (Min.) | Tank Temp. (° C.) | Bulb Temp. (° C.) | Pressure Gauge |
|---|---|---|---|---|
| 1 | 0 | 23.8 | 121.6 | 42.0 |
| 2 | 2 | 23.9 | 121.3 | 42.0 |
| 3 | 5 | 23.9 | 121.0 | 42.0 |
| 4 | 20 | 23.9 | 121.0 | 41.9 |
| 5 | 90 | 24.0 | 121.0 | 41.8 |
| 6 | 320 | 24.0 | 121.0 | 41.2 |
| 7 | 472 | 24.0 | 121.0 | 41.0 |
| 8 | 1378 | 24.0 | 121.0 | 39.2 |
| 9 | 1800 | 24.3 | 121.0 | 38.8 |
| 10 | 1910 | 24.3 | 121.0 | 38.6 |
| 11 | 2860 | 24.2 | 121.0 | 37.4 |
| 12 | 3000 | 24.2 | 121.0 | 37.5 |

Example 10

Oxidation of an Amido Acid in Sulfolane Without Antioxidant

Sulfolane (24.84 g) was placed in a 100 mL glass bulb apparatus under about 41 psig of pure oxygen. The temperature was maintained at 100° C. for 168 minutes and then raised to 120° C. and held there using a Eurotherm/thermocouple assembly for an additional 142 minutes. 5.0 g (16 wt %) amido acid from Example 1A was then added to the bulb and the temperature maintained at 120° C. for 490 min. Slight yellow coloration of solution was observed.

As depicted in Table 7 below, the data from the glass bulb test at 100° C. was measured at six different data points. The oil bath temperature for the glass bulb was then raised to 120° C. and four more data points were taken.

TABLE 7

| Data Point | Time (Min.) | Tank Temp. (° C.) | Bulb Temp. (° C.) | Pressure Gauge |
|---|---|---|---|---|
| 1 | 0 | 23.0 | 99.7 | 41.2 |
| 2 | 2 | 23.0 | 99.6 | 41.0 |
| 3 | 5 | 23.0 | 99.7 | 41.0 |
| 4 | 30 | 23.0 | 99.6 | 40.9 |
| 5 | 140 | 23.0 | 99.6 | 40.7 |
| 6 | 168 | 23.0 | 99.6 | 40.6 |
| 7 | 172 | 23.0 | 122.6 | 42.0 |
| 8 | 190 | 23.0 | 120.7 | 42.1 |

TABLE 7-continued

| Data Point | Time (Min.) | Tank Temp. (° C.) | Bulb Temp. (° C.) | Pressure Gauge |
|---|---|---|---|---|
| 9 | 210 | 23.0 | 120.6 | 42.0 |
| 10 | 310 | 23.0 | 120.8 | 41.8 |

As depicted in Table 8 below, once having added amido acid from Example 1A, the data from the glass bulb test at 120° C. was measured at twelve different data points.

TABLE 8

| Data Point | Time (Min.) | Tank Temp. (° C.) | Bulb Temp. (° C.) | Pressure Gauge |
|---|---|---|---|---|
| 1 | 0 | 22.5 | 120.8 | 41.2 |
| 2 | 2 | 22.5 | 120.7 | 41.0 |
| 3 | 5 | 22.5 | 120.7 | 40.9 |
| 4 | 20 | 22.5 | 120.7 | 40.8 |
| 5 | 50 | 22.8 | 120.5 | 40.6 |
| 6 | 130 | 22.8 | 120.5 | 40.3 |
| 7 | 185 | 22.8 | 120.5 | 39.9 |
| 8 | 230 | 22.8 | 120.7 | 39.8 |
| 9 | 325 | 22.8 | 120.5 | 39.3 |
| 10 | 375 | 22.9 | 120.7 | 39.0 |
| 11 | 425 | 23.0 | 120.8 | 38.8 |
| 12 | 490 | 23.0 | 120.8 | 38.5 |

Example 11

Oxidation of an Amido Acid in Sulfolane Without Antioxidant

The experiment of Example 10 was repeated, except 20.02 (44 wt %) amido acid from Example 1B was used. The amount of sulfolane, 25.29 g, was approximately the same as in Example 9. The 120° C. temperature was maintained for 445 min. 7.19 mmol $O_2$ was absorbed. It appeared that there was a rapid initial $O_2$ uptake, followed by rate decay.

The 7.19 mmol $O_2$ was calculated as follows: The bulb and amido acid weight 121.624 prior to oxygen absorption. After oxygen absorption the bulb and amido acid weight 121.6242. Thus, 230.1 mg $O_2$ absorption was observed which is 7.19 mmol $O_2$.

As depicted in Table 9 below, the data from the glass bulb test at 120° C. was measured at fourteen different data points.

TABLE 9

| Data Point | Time (Min.) | Tank Temp. (° C.) | Bulb Temp. (° C.) | Pressure Gauge |
|---|---|---|---|---|
| 1 | 0 | 24.2 | 122 | 42.7 |
| 2 | 2 | 24.2 | 121.8 | 42.5 |
| 3 | 5 | 24.2 | 121.6 | 42.2 |
| 4 | 24 | 24.2 | 121.2 | 41.7 |
| 5 | 54 | 24.2 | 121.2 | 41.3 |
| 6 | 92 | 24.3 | 121.3 | 39.2 |
| 7 | 124 | 25.0 | 121.2 | 36.8 |
| 8 | 150 | 24.5 | 121.2 | 35.0 |
| 9 | 178 | 24.5 | 121.3 | 33.0 |
| 10 | 220 | 24.5 | 121.3 | 30.4 |
| 11 | 300 | 25.5 | 121.0 | 26.5 |
| 12 | 344 | 24.5 | 121.2 | 24.9 |
| 13 | 396 | 24.8 | 121.0 | 23.0 |
| 14 | 445 | 25.0 | 121.3 | 21.7 |

Example 12

Oxidation of an Amido Acid in Sulfolane Without Antioxidant

The experiment of Example 11 was repeated, except 10.02 g (28 wt %) amido acid from Example 1D was used. The amount of sulfolane, 25.36 g, was approximately the same as in Example 9. The amido acid was added to sulfolane at 100° C. and maintained for about 1400 min. The temperature was then raised to 120° C. and maintained for an additional 180 min. There was negligible $O_2$ absorption over the 1580 min. period.

As depicted in Table 10 below, the data from the glass bulb test was measured at fifteen different data points. The first ten data points were measure at the 100° C. temperature and the last four at the 120° C. temperature.

TABLE 10

| Data Point | Time (Min.) | Tank Temp. (° C.) | Bulb Temp. (° C.) | Pressure Gauge |
|---|---|---|---|---|
| 1 | 0 | 24.6 | 101.4 | 40.0 |
| 2 | 2 | 24.6 | 101.3 | 39.7 |
| 3 | 5 | 24.6 | 101.0 | 39.6 |
| 4 | 24 | 24.6 | 100.8 | 39.5 |
| 5 | 75 | 24.6 | 100.8 | 39.5 |
| 6 | 150 | 24.7 | 101.0 | 39.5 |
| 7 | 270 | 24.9 | 101.2 | 39.5 |
| 8 | 346 | 25.0 | 101.0 | 39.4 |
| 9 | 402 | 25.0 | 101.1 | 39.3 |
| 10 | 1305 | 24.2 | 101.8 | 38.5 |
| 11 | 1400 | 24.2 | 100.8 | 28.5 |
| 12 | 1410 | 24.5 | 120.8 | 39.8 |
| 13 | 1420 | 24.5 | 119.9 | 39.7 |
| 14 | 1494 | 24.2 | 121.4 | 39.8 |
| 15 | 1580 | 24.2 | 121.4 | 39.8 |

Example 13

Oxidation of Methyl Ester of an Amido Acid Without Antioxidant

The methyl ester of an amido acid was prepared using 271.4 g of the amido acid of Example 1E mixed with 118.97 g thionyl chloride in 100 mL methylene chloride. The solution was allowed to stand overnight. The next day 50 mL methanol was slowly added dropwise with stirring and then allowed to stand. Some exotherm and boiling of the methylene chloride occurred. 25 g sodium hydroxide dissolved in 120 mL water was slowly added dropwise and there was some reflux of the methylene chloride. The methylene chloride layer was then isolated using a separatory funnel, washed once with water, and dried with anhydrous sodium sulfate. The methylene chloride was then removed using a rotovap.

46.24 g crude methyl ester product was obtained. 6.67 g was then recrystallized from 10 mL −10° C. methanol, and then washed with −70° C. methanol, yielding 4.78 g.

The methyl ester of an amido acid (206.7 mg) was placed in a 70 mL bulb at approximately 40 psi oxygen and held at 120° C. for 19 hours. The bulb was then cooled and vented. The yellow product appeared to show a weight gain of 7.0 mg.

Example 14

Oxidation of Methyl Ester of an Amido Acid Without Antioxidant

The recrystallized methyl ester of an amido acid from Example 13 (3.0 g) was put in a 70 mL oxidation bulb at 120° C. 0.841 mmol $O_2$ was absorbed and there was much less than an 8.0% conversion. The yield of the recrystallized methyl ester was 16%. The product was a light yellow color.

As depicted in Table 11 below, the data from the glass bulb test was measured at ten different data points.

TABLE 11

| Data Point | Time (Min.) | Tank Temp. (° C.) | Bulb Temp. (° C.) | Pressure Gauge |
|---|---|---|---|---|
| 1 | 0 | 24.0 | 121.0 | 35.5 |
| 2 | 2 | 24.0 | 120.8 | 35.5 |
| 3 | 5 | 24.0 | 120.6 | 35.4 |
| 4 | 30 | 24.0 | 120.4 | 35.1 |
| 5 | 73 | 24.0 | 120.5 | 34.9 |
| 6 | 100 | 24.0 | 120.5 | 34.6 |
| 7 | 194 | 24.0 | 120.6 | 33.9 |
| 8 | 260 | 24.0 | 120.4 | 33.5 |
| 9 | 315 | 24.0 | 120.4 | 33.3 |
| 10 | 345 | 24.0 | 120.5 | 33.1 |

Example 15

Oxidation of Crystalline Sodium Nonanamidohexanoyloxybenzenesulfonate at 100° C. or 120° C. Without Antioxidant 2.50 g crystalline sodium nonanamidohexanoyloxybenzenesulfonate was placed in each of two Schott bottles. The temperature was held at 100° C. or 120° C. for 16 hours using a Eurotherm/thermocouple assembly to maintain the temperature. Oxidation was measured using a MicroOxymax with one atmosphere of air. The crystalline amido acid gave slight $O_2$ uptake and showed no discoloration at either temperature.

Example 16

Oxidation of Aqueous Sodium Nonanamidohexanoyloxybenzenesulfonate Without Antioxidant A sample of sodium nonanamidohexanoyloxybenzenesulfonate recrystallized from water (9.94 g) was dissolved in 20.41 g water and put in a 104 mL bulb. The solution was stirred with $O_2$ at approximately 120° C. for 312 min. The solution showed a weight gain of about 7.5 mg.

As depicted in Table 12 below, the data from the glass bulb test was measured at ten different data points.

TABLE 12

| Data Point | Time (Min.) | Tank Temp. (° C.) | Bulb Temp. (° C.) | Pressure Gauge |
|---|---|---|---|---|
| 1 | 0 | 23.0 | 121.7 | 54.0 |
| 2 | 2 | 23.0 | 121.4 | 57.0 |
| 3 | 5 | 23.0 | 121.2 | 58.0 |
| 4 | 10 | 23.0 | 120.9 | 58.2 |
| 5 | 40 | 23.0 | 121.0 | 57.3 |
| 6 | 134 | 23.0 | 121.8 | 56.8 |
| 7 | 175 | 23.0 | 120.9 | 56.5 |
| 8 | 205 | 23.0 | 120.8 | 56.5 |
| 9 | 235 | 23.0 | 120.8 | 56.2 |
| 10 | 312 | 23.0 | 121.0 | 55.5 |

Example 17

Oxidation of Aqueous SPS Without Antioxidant

Sodium phenol sulfonate (SPS) (10.13 g) was fully dissolved in 10.76 g water. The solution was stirred with $O_2$ at approximately 120° C. for 1200 min. The solution showed a weight loss of about 2.0 mg from water vapor loss. The product was a light yellow color.

The following table is a summary of the results of Examples 2–12 and 14–17.

TABLE 13

| Example | Substrate | Inhibitor | Phase/Solvent | Temp Time | Measuring Apparatus | Results |
|---|---|---|---|---|---|---|
| 2 | Amido Acid | — | Crystalline | 80° C. 24 hours | MicroOxymax | Negligible $O_2$ absorption. |
|  |  |  | Melt | 100° C. 24 hours |  | Strong $O_2$ absorption by melt. |
| 3 | Amido Acid | — | Neat melt | 100° C. 80 hours | MicroOxymax | Usual $O_2$ consumption by uninhibited sample. |
|  |  | 3.6 mg Ethanox 330 ® |  | 100° C. 80 hours |  | Slight consumption of $O_2$ by inhibited sample; no discoloration. |
| 4 | Amido Acid | — | Neat melt | 100° C. 72 hours | MicroOxymax | Strong oxidation by uninhibited sample. |
|  |  | 0.35 wt % BHT |  | 100° C. 72 hours |  | No oxidation. |
| 5 | Amido Acid | — | Neat melt | 100° C. 63 hours | MicroOxymax | Substantial $O_2$ consumed. |
|  | Methyl Ester of Amido Acid | — | Neat melt | 100° C. 63 hours | MicroOxymax | Little $O_2$ consumed. |
| 6 | Amido Acid | — | Neat melt | 100° C. 1786 min | Glass bulb, Pressure drop apparatus | Moderate initial rate followed by rate decay. Conversion = 5.6% in 1786 minutes, yellow/brown product. |
| 7 | Amido Acid | — | Neat melt | 120° C. 250 min | Glass bulb, Pressure drop apparatus | Strong $O_2$ uptake. 4.8% conversion, and light brown product. |
| 8 | Amido Acid | — | Neat melt | 120° C. 430 min | Glass bulb, Pressure drop apparatus | Rapid initial $O_2$ uptake followed by rate decay. 7.4% conversion and light brown product. |
| 9 | Amido Acid | — | Neat melt | 100° C. 2820 min 120° C. 3000 min | Glass bulb, Pressure drop apparatus | Good initial rate of $O_2$ uptake with subsequent decay in $O_2$ uptake rate at each temperature (autoretardation). Very low $RO_2H$ yield (0.5%). Yellow/brown product color. |

TABLE 13-continued

| Example | Substrate | Inhibitor | Phase/Solvent | Temp Time | Measuring Apparatus | Results |
|---|---|---|---|---|---|---|
| 10 | 16 wt % Amido Acid | — | Sulfolane Solvent | 120° C. 490 min | Glass bulb, Pressure drop apparatus | Negligible consumption of $O_2$ |
| 11 | 44 wt % Amido Acid | — | Sulfolane Solvent | 120° C. 445 min | Glass bulb, Pressure drop apparatus | Rapid initial $O_2$ uptake followed by rate decay. 9.7% conversion with yellow product, high (44%) $RO_2H$ yield. |
| 12 | 28 wt % Amido Acid | — | Sulfolane Solvent | 100° C. 0–1400 min 120° C. 1400–1580 min | Glass bulb, Pressure drop apparatus | No significant $O_2$ uptake at 100° C. or 120° C. until addition of 0.22% in t-$Bu_2O_2$ (free radical initiator) at 12° C., then rapid oxidation. Very low $RO_2H$ yield (3.4%). |
| 14 | Methyl Ester of Amido Acid | — | Neat melt | 120° C. 345 min | Glass bulb, Pressure drop apparatus | Conversion <8%, slight decay in rate, very light yellow color formation, $RO_2H$ yield = 16%. |
| 15 | Sodium Nonanamido Hexanoyloxy benzene sulfonate | — | Crystalline | 120° C. 16 hours 100° C. 16 hours | MicroOxymax | No significant $O_2$ uptake. No significant $O_2$ uptake. |
| 16 | 33 wt % Sodium Nonanamido hexanoyloxy benzene-sulfonate | — | Water | 120° C. 312 min | Glass bulb, Pressure drop apparatus | Slight $O_2$ absorption and discoloration. |
| 17 | 50 wt % sodium Phenol Sulfonate (SPS) | — | Water | 120° C. 1200 min | Glass bulb, Pressure drop apparatus | Very small $O_2$ uptake. |

The claimed invention is:

1. A stabilized amido acid composition comprising an effective stabilizing amount of an antioxidant and an amido acid of formula I or II:

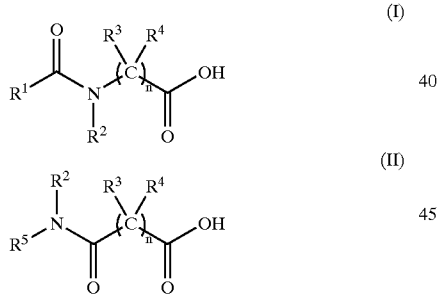

wherein $R^1$ is selected from $C_1$-$C_{22}$ alkyl, $C_2$-$C_{22}$ alkenyl, $C_2$-$C_{22}$ alkynyl, $C_3$-$C_{22}$ cycloalkyl, and $C_6$-$C_{14}$ aryl;

$R^2$ and $R^5$ are each independently selected from hydrogen, $C_1$-$C_{22}$ alkyl, $C_2$-$C_{22}$ alkenyl, $C_2$-$C_{22}$ alkynyl, $C_3$-$C_{22}$ cycloalkyl, $C_6$-$C_{14}$ aryl, and where in formula II, $R^2$ and $R^5$ can together with the nitrogen carrying them form a $C_3$-$C_{10}$ heterocycle;

$R^3$ and $R^4$ are each independently selected from hydrogen, $C_1$-$C_{10}$ alkyl, $C_2$-$C_{10}$ alkenyl, $C_2$-$C_{10}$ alkynyl, $C_3$-$C_{10}$ cycloalkyl, $C_6$-$C_{10}$ aryl and where $R^3$ and $R^4$ can together with the carbon carrying them form a $C_3$-$C_{10}$ cycloalkyl; and n is an integer from 0 to 20.

2. The composition of claim 1, wherein $R^1$ is selected from $C_5$-$C_{15}$ alkyl, $C_5$-$C_{15}$ alkenyl, $C_5$-$C_{15}$ alkynyl, $C_5$-$C_{15}$ cycloalkyl, and $C_6$-$C_{14}$ aryl;

$R^2$ and $R^5$ are each independently selected from hydrogen, $C_5$-$C^{15}$ alkyl, $C_5$-$C^{15}$ alkenyl, $C_5$-$C_{15}$ alkynyl, $C_5$-$C_{15}$ cycloalkyl, $C_6$-$C_{14}$ aryl, and where in formula II, $R^2$ and $R^5$ together with the nitrogen carrying them can form a $C_3$-$C_{10}$ heterocycle;

$R^3$ and $R^4$ are each independently selected from hydrogen, $C_1$-$C_5$ alkyl, $C_2$-$C_5$ alkenyl, $C_2$-$C_5$ alkynyl, $C_3$-$C_6$ cycloalkyl, $C_6$-$C_{10}$ aryl and where $R^3$ and $R^4$ can together with the carbon carrying them form a $C_3$-$C_6$ cycloalkyl; and n is an integer from 0 to 10.

3. The composition of claim 1, wherein $R^1$ is a $C_5$-$C_{15}$ alkyl;

$R^2$ and $R^5$ are each hydrogen or $C_5$-$C_{15}$ alkyl;

$R^3$ and $R^4$ are each hydrogen; and n is an integer from 2 to 10.

4. The composition of claim 1, wherein the antioxidant is a phenolic antioxidant or mixture of phenolic antioxidants.

5. The composition of claim 1, wherein the antioxidant is selected from 1,3,5-trimethyl-2,4,6-tris (3,5-di-tert-butyl-4-hydroxybenzyl) benzene, tetrakis(methylene (3,5-di-tert-butyl-4-hydroxyhydrocinnamate)) methane, and butylated hydroxytoluene (BHT).

6. The composition of claim 1, wherein the stabilized amido acid composition does not exhibit visible discoloration after heating it for about 72 hours at 100° C.

7. The composition of claim 1, wherein the stabilizing effective amount of antioxidant ranges from about 0.001 to about 2% by weight.

8. The composition of claim 1, wherein the stabilized amido acid composition is a liquid, a liquid melt, or a solution.

9. A process for preparing a stabilized amido acid composition comprising admixing a stabilizing effective amount of an antioxidant and an amido acid of formula I or formula II:

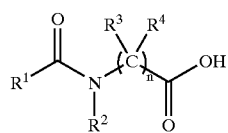

(I)

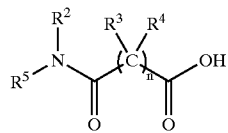

(II)

wherein $R^1$ is selected from $C_1$-$C_{22}$ alkyl, $C_2$-$C_{22}$ alkenyl, $C_2$-$C_{22}$ alkynyl, $C_3$-$C_{22}$ cycloalkyl, and $C_6$-$C_{14}$ aryl;

$R^2$ and $R^5$ are each independently selected from hydrogen, $C_1$-$C_{22}$ alkyl, $C_2$-$C_{22}$ alkenyl, $C_2$-$C_{22}$ alkynyl, $C_3$-$C_{22}$ cycloalkyl, $C_6$-$C_{14}$ aryl, and where in formula II, $R^2$ and $R^5$ can together with the nitrogen carrying them form a $C_3$-$C_{10}$ heterocycle;

$R^3$ and $R^4$ are each independently selected from hydrogen, $C_1$-$C_{10}$ alkyl, $C_2$-$C_{10}$ alkenyl, $C_2$-$C_{10}$ alkynyl, $C_3$-$C_{10}$ cycloalkyl, $C_6$-$C_{10}$ aryl and where $R^3$ and $R^4$ together with the carbon carrying them form a $C_3$-$C_{10}$ cycloalkyl; and n is an integer from 0 to 20.

10. The process of claim 9, wherein the amido acid is in a liquid state, a molten state, or in solution when admixed with the antioxidant.

11. The process of claim 9, wherein the antioxidant is selected from 1,3,5-trimethyl-2,4,6-tris (3,5-di-tert-butyl-4-hydroxybenzyl) benzene, tetrakis(methylene (3,5-di-tert-butyl-4-hydroxyhydrocinnamate)) methane, and butylated hydroxytoluene (BHT).

12. The process of claim 9, wherein the effective stabilizing amount of the antioxidant ranges from about 0.001 to about 2% by weight.

* * * * *